United States Patent [19]

Koda et al.

[11] Patent Number: 4,670,583
[45] Date of Patent: Jun. 2, 1987

[54] AMIDE COMPOUNDS

[75] Inventors: Akihide Koda; Mikio Hori, both of Gifu; Mitsugi Yasumoto, Tokushima; Naosuke Matsuura, Gifu; Ichiro Yamawaki; Yukio Tada, both of Tokushima, all of Japan

[73] Assignee: Taiho Pharmaceutical Company, Limited, Tokyo, Japan

[21] Appl. No.: 772,857

[22] Filed: Sep. 5, 1985

[30] Foreign Application Priority Data

Sep. 12, 1984 [JP] Japan .................................. 59-191988

[51] Int. Cl.$^4$ .................. C07C 149/40; C07C 103/38; C07C 103/58
[52] U.S. Cl. .................................. 562/426; 564/207; 564/223
[58] Field of Search ................ 562/426; 564/207, 223; 514/562, 627, 629

[56] References Cited

U.S. PATENT DOCUMENTS 3,235,456  2/1966  Thominet et al. ............... 564/223 X
4,442,117  4/1984  Kunz et al. ..................... 562/426 X
4,579,970  4/1986  Hietaniemi et al. ............... 564/223

Primary Examiner—Werren B. Lone
Assistant Examiner—Vera C. Clarke
Attorney, Agent, or Firm—Murray and Whisenhunt

[57] ABSTRACT

This invention provides an amide compound represented by the formula

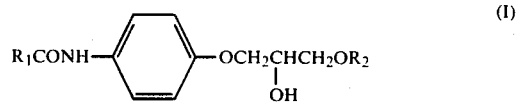

(I)

wherein $R_1$ is vinyl, 2-(methylsulfinyl)ethyl, 2-(methylsulfonyl)ethyl, 2-(2-acetylamino-2-carboxyethylthio)ethyl or 2-[2-(4-amino-4-carboxybutyrylamino)-2-(carboxymethylcarbamoyl)ethylthio]ethyl and $R_2$ is hydrogen or lower alkyl, process for the preparation thereof, and antiallergic compositions cotaining the amide compound.

8 Claims, No Drawings

AMIDE COMPOUNDS

This invention relates to novel amide compounds and process for preparing the amide compounds, and also to pharmaceutical compositions, more particularly antiallergic composition containing the amide compounds.

The amide compounds of this invention are novel compounds undisclosed in literature and are represented by the following formula

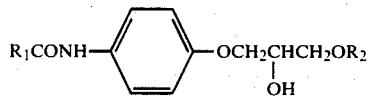

wherein $R_1$ is vinyl, 2-(methylsulfinyl)ethyl, 2-(methylsulfonyl)ethyl, 2-(2 acetylamino-2-carboxyethylthio)ethyl or 2-[2-(4-amino-4-carboxybutyrylamino)-2-(carboxymethylcarbamoyl)ethylthio]ethyl and $R_2$ is hydrogen or lower alkyl.

Examples of lower alkyl groups represented by $R_2$ in the formula (I) are alkyl groups having 1 to 6 carbon atoms such as methyl, ethyl, propyl, isopropyl, butyl, pentyl, hexyl and the like.

We synthesized the amide compounds of the formula (I) and found that the compounds have antiallergic action and thus are useful as pharmaceuticals. This invention has been accomplished based on this novel finding.

The compounds of the formula (I) can be prepared by the processes as shown below in the following reaction equations.

Reaction Equation I

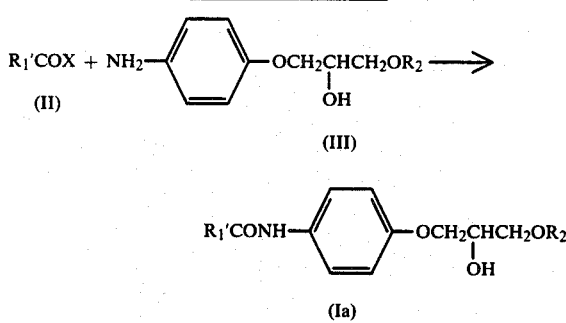

In the foregoing formulas, $R_1'$, is vinyl, 2-(methylsulfinyl)ethyl or 2-(methylsulfonyl)ethyl, $R_2$ is as defined above and X is halogen atom such as chlorine, bromine, iodine and the like.

According to Reaction Equation I, the acid halide (II) is reacted with the amine derivative (III) to give the amide compound (Ia) of the invention. The reaction is conducted without using a solvent or in a suitable solvent, preferably in the presence of a basic compound, at a temperature in the range of about 0° to about 150° C. and is completed in about 0.5 to about 10 hours. Examples of suitable solvents are those which do not adversely affect the reaction and include $C_1$-$C_2$ halogenated hydrocarbons such as chloroform, dichloromethane, dichloroethane and the like; cyclic ethers such as tetrahydrofuran, dioxane and the like; di($C_1$-$C_6$ alkyl)ethers such as diethyl ether, dibutyl ether and the like; aromatic hydrocarbons such as benzene, toluene, xylene and the like; di($C_1$-$C_6$ alkyl)ketones such as acetone, methyl ethyl ketone and the like; esters of $C_1$-$C_3$ saturated aliphatic alcohol with $C_1$-$C_3$ saturated fatty acid such as ethyl acetate, methyl acetate and the like; and polar solvents such as dimethylformamide, dimethylsulfoxide and the like; water; and mixtures of these solvents. Examples of basic compounds are inorganic compounds including alkali metals such as sodium and potassium, hydrides of these alkali metals such as sodium hydride and potassium hydride, hydroxides of alkali metals such as sodium hydroxide and potassium hydroxide, carbonates of alkali metals such as sodium carbonate and potassium carbonate, and hydrogencarbonates of alkali metals such as sodium hydrogencarbonate and potassium hydrogencarbonate, and secondary or tertiary organic amines including pyridine, morpholine, piperidine, piperazine and triethylamine and the like. The acid halide (II) is used in an excess amount relative to the amine derivative (III), preferably in an amount of about 1 to about 4 moles per mole of the amine derivative (III). The basic compound is used in an excess amount relative to the acid halide (II), preferably in an amount of about 1 to about 4 moles per mole of the acid halide (II).

The acid halides (II) useful in the process of Reaction Equation I are known compounds and are readily available. Also amine derivatives (III) which can be used in the process are also known in the art, and can be prepared, for example, by the process disclosed in Japanese Unexamined Patent Publication No. 44737/1984 (published on Aug. 18, 1984).

Reaction Equation II

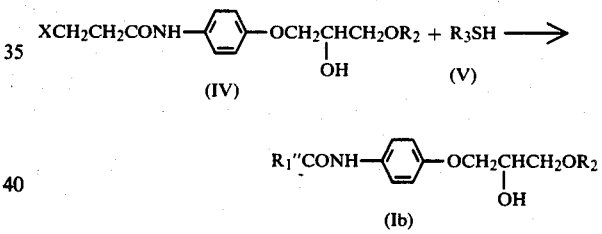

In the foregoing formulas, $R_3$ is 2-acetylamino-2-carboxyethyl or 2-(4-amino 4-carboxybutyrylamino)- 2-(carboxymethylcarbamoyl)ethyl, $R_1''$ is 2-(2-acetylamino 2-carboxyethylthio)ethyl or 2-[2-(4-amino-4-carboxybutyrylamino)-2-(carboxymethylcarbamoyl)ethylthio]ethyl, and $R_2$ and X are as defined above.

According to Reaction Equation II, the halide compound (IV) is reacted with the thiol compound (V) to give the amide compound (Ib) of the present invention. The reaction is effected in a suitable solvent, preferably in the presence of a basic compound, at a temperature of about $-10°$ to about $-100°$ C. and is completed in about 0.5 to about 10 hours. Useful solvents include the cyclic ethers, dialkyl ethers, aromatic hydrocarbons, polar solvents and water as exemplified above with respect to Reaction Equation I, and further include $C_1$-$C_6$ monohydric saturated aliphatic alcohols such as methanol, ethanol and the like, and mixtures of these solvents. The basic compounds enumerated above as useful in the process of Reaction Equation I can be used with good results in the process of Reaction Equation II. The halide compound (IV) is used in an excess amount relative to the thiol compound (V), preferably in an amount of about 1 to about 4 moles per mole of the thiol compound (V). The basic compound is used in an excess amount relative to the halide compound (IV), preferably in an amount of about 1 to about 4 moles per mole of the halide compound (IV).

The halide compounds (IV) can be prepared by reacting the amine compound (III) serving as the starting compound with the 3-halogenopropionic acid halide represented by the formula

XCH$_2$CH$_2$COZ  (VI)

wherein X is as defined above and Z is halogen atom such as chlorine, bromine and iodine. The reaction is performed in the foregoing solvent, preferably in the presence of the aforesaid basic compound at a temperature of about $-10°$ to about $100°$ C. and is completed in about 0.5 to about 10 hours. The amount of the 3-halogenopropionic acid halide (VI) is about 1 to about 2 moles per mole of the amine compound (III). The basic compound is used in an excess amount relative to the amine compound (III), preferably in an amount of about 1 to about 4 moles per mole of the amine compound (III). The thiol compounds (V) are known compounds.

The compounds of the present invention prepared by the processes of Reaction Equations I and II can be separated from the reaction mixture by conventional separation methods such as recrystallization, extraction, distillation and concentration and column chromatography.

For use as drugs, the compounds of the present invention can be given to mammals including humans in the form of pharmacological compositions having various dosage forms, such as oral preparation, injection, rectal suppository or inhalant, in accordance with the purpose of therapy contemplated. Such preparations can be formulated in the manner already known in the art, using conventional pharmacologically acceptable, non-toxic carriers or excipients. For the formulation of solid preparations for oral administration, such as tablets, coated tablets, granules, powders and capsules, excipients and, when required, binders, disintegrators, lubricants or glazes, coloring agents, corrigents, etc. can be added to the compound of this invention. Such additives are already known in the art and useful examples are excipients such as lactose, white sugar, sodium chloride, glucose solution, starch, calcium carbonate, kaolin, crystalline cellulose and silicic acid: binders such as water, ethanol, propanol, glucose, carboxymethylcellulose, shellac, methylcellulose, potassium phosphate and polyvinylpyrrolidone; disintegrators such as dried starch, sodium alginate, agar powder, sodium hydrogencarbonate, calcium carbonate, sodium lauryl sulfate, glyceryl monostearate, starch and lactose; lubricants or glazes such as purified talc, steraric acid salt, boric acid powder, solid polyethylene glycol; corrigents such as sucrose, compound bitter orange peel, citric acid, tartaric acid, etc. For the formulation of liquid preparations for oral administration, such as solutions for oral administration, syrups, etc., conventional corrigents, buffers, stabilizers, etc. can be added to the present compound. Such preparations can be formulated in the usual manner. Examples of useful corrigents are those exemplified above. Typical buffers include sodium citrate. Stabilizers include tragacanth, gum arabic, gelatin, etc. The pharmacological compositions thus prepared are orally administered. Parenteral solutions can be formulated in the usual manner using distilled water for injection as the carrier and adding to the present compound conventional additives such as pH-adjusting agents, buffers, stabilizers, isotonic agents, local anesthetics, etc. Examples of the pH-adjusting agents and buffers are sodium salts of citric acid, acetic acid and phosphoric acid. The stabilizers include sodium pyrosulfite (anti-oxidant), EDTA, thioglycolic acid, thiolactic acid, etc. Examples of useful local anesthetics are procaine hydrochloride, xylocaine hydrochloride, lidocaine hydrochloride, etc. Such solutions can be given subcutaneously, intramascularly or intravenously. For the preparation of rectal suppositories, conventional excipients such as fatty acid triglyceride and like base and if required, Tween and like surfactants, etc. can be added to the present compound, followed by formulation in the usual manner. Such suppositories are administered to the rectum. Inhalants can be prepared in the usual manner by adding to the present compound a conventional propellant such as flon gas, etc., and other conventional additives, if desired.

The amount of the present compound to be incorporated into the foregoing preparations varies with the symptoms of the patient or with the type of the preparation. Preferably the amount per administration unit is about 5 to about 1000 mg for oral administration, about 0.1 to about 500 mg for parenteral administration, about 5 to about 1000 mg for intrarectal administration and about 1 to about 500 mg for inhalant administration. The dosage per day for an adult, which is variable with the symptoms, age, and the like, is preferably about 0.1 to about 5000 mg for usual purposes.

The present invention will be described below in more detail with reference to the following Examples.

EXAMPLE 1

Preparation of N-[4-(3-ethoxy-2 hydroxypropoxy)phenyl] acrylamide (Compound 1)

A 2.11 g quantity of 4 (3-ethoxy 2-hydroxypropoxy)aniline and 1.52 g of triethylamine were dissolved in 30 ml of dichloromethane. To the solution was added 0.91 g of acryl chloride with ice cooling. The mixture was stirred at room temperature for 4 hours and the reaction mixture was concentrated. The residue was extracted with ethyl acetate. The ethyl acetate layer was washed with water and concentrated. The residue was recrystallized from ethyl ether, giving 2.45 g of N [4 (3 ethoxy-2-hydroxypropoxy)phenyl]acrylamide in a yield of 92.5 %. M.p. 125° to 126° C.

| Elementary analysis (for $C_{14}H_{19}NO_4$) | | |
| --- | --- | --- |
| C | H | N |
| Calcd. (%) 63.38 | 7.22 | 5.28 |
| Found (%) 63.15 | 7.16 | 5.14 |

EXAMPLE 2

Preparation of N-[4-(3-ethoxy-2-hydroxypropoxy)phenyl]-3-(methylsulfinyl)propionamidne (Compound 2)

A 2.11 g quantity of 4-(3-ethoxy-2-hydroxypropoxy)aniline and 1.53 g of triethylamine were dissolved in 50 ml of dichloromethane. To the solution was added 1.55 g of 3-(methylsulfinyl)propionyl chloride with ice cooling. The mixture was stirred at room temperature for 2 hours. The reaction mixture was washed with water, dewatered with Glauber's salt and concentrated. The residue was recrystallized from acetonitrile, giving 2.95 g of N-[4-(3-ethoxy-2-hydroxyperopoxy)phenyl]-3-

(methylsulfinyl)propionamide in a yield of 89.7 %. M.p. 112° to 113.5° C.

| Elementary analysis (for $C_{15}H_{23}NO_5S$) | | | |
|---|---|---|---|
|  | C | H | N |
| Calcd. (%) | 54.69 | 7.04 | 4.25 |
| Found (%) | 54.61 | 7.19 | 4.37 |

EXAMPLE 3

Preparation of N-[4-(2,3-dihydroxypropoxy)phenyl]-3-(methylsulfinyl)propionamide (Compound 3)

A 1.83 g quantity of 4-(2,3-dihydroxypropoxy)aniline and 1.53 g of triethylamine were dissolved in 30 ml of dimethylformamide. To the solution was added 1.55 g of 3-(methylsulfinyl)propionyl chloride with ice cooling. The same subsequent procedure as in Example 2 was repeated and recrystallization from ethanol was effected, giving 2.42 g of N-[4-(2,3-dihydroxypropoxy)-phenyl]-3-(methylsulfinyl)propionamide in a yield of 80.4%. M.p. 139° to 141° C.

| Elementary analysis (for $C_{13}H_{19}NO_5S$) | | | |
|---|---|---|---|
|  | C | H | N |
| Calcd. (%) | 51.81 | 6.35 | 4.65 |
| Found (%) | 51.61 | 6.24 | 4.50 |

EXAMPLE 4

Preparation of N-[4-(3-ethoxy-2-hydroxypropoxy)phenyl]-3-(methylsulfonyl)propionamide (Compound 4)

A 2.11 g quantity of 4-(3-ethoxy-2-hydroxypropoxy)aniline and 1.53 g of triethylamine were dissolved in 50 ml of dichloromethane. To the solution was added 1.71 g of 3-(methylsulfonyl)propionyl chloride with ice cooling. The same subsequent procedure as in Example 2 was repeated and recrystallization from benzene was performed, giving 3.25 g of N-[4-(3-ethoxy-2-hydroxypropoxy)phenyl]-3-(methylsulfonyl)propionamide in a yield of 94.2 %. M.p. 111° to 112° C.

| Elementary analysis (for $C_{15}H_{23}NO_6S$) | | | |
|---|---|---|---|
|  | C | H | N |
| Calcd. (%) | 52.16 | 6.71 | 4.06 |
| Found (%) | 52.39 | 6.68 | 4.02 |

EXAMPLE 5

Preparation of N-[4-(2,3-dihydroxypropoxy)phenyl]-3-(methylsulfonyl)propionamide (Compound 5)

A 1.83 g quantity of 4 (2,3-dihydroxypropoxy)aniline and 1.53 g of triethylamine were dissolved in 30 ml of dimethylformamide. To the solution was added 1.71 g of 3-(methylsulfonyl)propionyl chloride with ice cooling. The same subsequent procedure as in Example 3 was repeated, thereby producing 2.80 g of N-[4-(2,3-dihydroxypropoxy)phenyl]-3-(methylsulfonyl)propionamide in a yield of 88.3 %. M.p. 160° to 161.5° C.

| Elementary Analysis (for $C_{13}H_{19}NO_6S$) | | | |
|---|---|---|---|
|  | C | H | N |
| Calcd. (%) | 49.20 | 6.03 | 4.41 |
| Found (%) | 49.06 | 6.08 | 4.21 |

EXAMPLE 6

Preparation of N-[4-(3-ethoxy-2-hydroxypropoxy)phenyl]-3-(2-acetylamino-2-carboxyethylthio)propionamide (Compound 6)

A 1.63 g quantity of L-acetylcysteine was dissolved in 0.80 g of sodium hydroxide and 50 ml of a 70% aqueous solution of ethanol with ice cooling. To the solution was added 3.02 g of N-[4-(3-ethoxy-2-hydroxypropoxy)phenyl]-3-chloropropionamide. The mixture was stirred at room temperature for 1 hour. The reaction mixture was concentrated and the residue was adjusted to a pH of 3 with diluted hydrochloric acid, washed with chloroform and extracted with ethyl acetate. The ethyl acetate layer was dewatered with Glauber's salt and was concentrated. The residue was purified with acetone-ether, giving 3.95 g of N-] 4-(3-ethoxy-2-hydroxypropoxy)phenyl]-3-(2-acetylamino-2 carboxyethylthio)propionamide in a yield of 92.1 %.

NMR(DMSO—$d_6$, δ, ppm)

1.10(3H, C$\underline{H}_3$CH$_2$O—), 1.86(3H, CH$_3$CO—), 2.4–2.7(2H, —SCH$_2$CH$_2$—), 3.7–4.0(3H, —⟨phenyl⟩—OCH$_2$CHCH$_2$—), 4.2–4.5(1H, —SCH$_2$C$\underline{H}$COOH), 6.86, 7.48(4H, —⟨phenyl⟩—O—), 8.24(1H, CH$_3$CON$\underline{H}$—), 9.82(1H, —CON$\underline{H}$—⟨phenyl⟩—O—)

EXAMPLE 7

Preparation of N-[4-(3-ethoxy 2-hydroxypropoxy)phenyl)]-3-[2-(4-amino-4-carboxybutyrylamino)-2-(carboxymethylcarbamoyl)ethylthio]propionamide (Compound 7)

A 5.73 g quantity of L-glutathione was dissolved in 1.20 g of sodium hydroxide and 300 ml of a 80% aqueous solution of methanol were dissolved with ice cooling. To the solution was added 3.02 g of N-]4-(3-ethoxy-2-hydroxypropoxy)phenyl]-3-chloropropionamide. The mixture was stirred at room temperature for 2 hours and the reaction mixture was concentrated. The residue was adjusted to a pH of 3.5 with diluted hydrochloric acid and filtered. The crystals thus obtained were recrystallized from a 50 % solution of methanol, giving 5.40 g of N-[4-(3-ethoxy-2-hydroxypropoxy)phenyl]-3-[2-(4-amino-4-carboxybutyrylamino)-2(carboxymethylcarbamoyl)ethylthio] propionamide in a yield of 94.2% M.p. 212° to 213.5° C.

| Elementary Analysis (for $C_{24}H_{36}N_4O_{10}S$) | | | |
|---|---|---|---|
| | C | H | N |
| Calcd. (%) | 50.34 | 6.34 | 9.78 |
| Found (%) | 50.21 | 6.40 | 9.75 |

Given below are examples of pharmacological compositions prepared by using the compounds of the present invention.

Preparation 1: Tablets

Tablets were prepared from the following composition (300 mg per tablet).

| Compound 1 | 100 mg |
|---|---|
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Fatty acid glyceride | 2 mg |
| Titanium dioxide | 2 mg |
| Total: | 300 mg |

Preparation 2: Granules

A granular preparation was formulated from the following composition (1000 mg per wrapper).

| Compound 1 | 200 mg |
|---|---|
| Mannitol | 540 mg |
| Corn starch | 100 mg |
| Crystalline cellulose | 100 mg |
| Hydroxypropyl cellulose | 50 mg |
| Talc | 10 mg |
| Total: | 1000 mg |

Preparation 3: Particles

A particulate preparation was formulated from the following composition (1000 mg per wrapper).

| Compound 2 | 200 mg |
|---|---|
| Mannitol | 520 mg |
| Corn starch | 100 mg |
| Crystalline cellulose | 100 mg |
| Hydroxypropyl cellulose | 70 mg |
| Talc | 10 mg |
| Total: | 1000 mg |

Preparation 4: Capsules

An encapsulated preparation was formulated from the following composition (250 mg per capsule).

| Compound 3 | 100 mg |
|---|---|
| Lactose | 50 mg |
| Corn starch | 47 mg |
| Crystalline cellulose | 50 mg |
| Talc | 2 mg |
| Magnesium stearate | 1 mg |
| Total: | 250 mg |

Preparation 5: Syrup

A 100 ml quantity of syrup was prepared from the following composition.

| Compound 4 | 1 g |
|---|---|
| Purified white sugar | 60 g |
| Ethyl p-hydroxybenzoate | 5 mg |
| Butyl p-hydroxybenzoate | 5 mg |
| Flavour | Adequate amount |
| Coloring agent | Adequate amount |
| Purified water | Adequate amount |
| Total: | 100 ml |

Preparation 6: Injection solution

An injection solution was prepared from the following composition (2 ml per ampule).

| Compound 1 | 100 mg |
|---|---|
| Distilled water for injection | Adequate amount |
| Total: | 2 ml |

Preparation 7: Suppositories

Suppositories were prepared from the following composition (1500 mg per piece).

| Compound 1 | 100 mg |
|---|---|
| Fatty acid triglyceride (available under the trademark "Witepsol W-35", product of Dynamit Nobel A.G., West Germany) | 1400 mg |
| Total: | 1500 mg |

Preparation 8: Inhalant

A 10 g quantity of inhalant was prepared from the following composition.

| Compound 1 | 100 mg |
|---|---|
| Sorbitan monooleate | 10 mg |
| Flon 12 | 9890 mg |
| Total: | 10 g |

Compounds of this invention were tested for pharmacological activity and acute toxicity, with the following results.

(1) Effect on passive cutaneous anaphylaxis (PCA)

A homocytotropic antibody for use in this test was produced according to the method of Tada et al (Journal of Immunology 106, 1002 (1971)) by immunizing a Wister rat with DNP-As (a product prepared by coupling dinitrophenyl group to an extract of Ascaris suum) and with pertussis vaccine. A serum containing the homocytotropic antibody was intracutaneously injected at four points of the shaven back of the male Wister rats weighing 180 to 200 g. Fourty-eight hours after the injection, 1 ml of a physiological saline containing 2.0 mg of DNP-As and 2.5 mg of Evans blue was injected to induce response, and the rats were dehematized to death in 30 minutes. The amount of the diffusion of the dye was measured according to the method of Katayama et al (Microbiology and Immunology 22, 89 (1978)) and the measured values were used as an index for PCA. Compound 1 was orally administered to the rats 30 minutes prior to the antigen challenge.

Percent PCA inhibition of Compound 1 was 24.0% at a dose of 5 mg/kg and 37.9% at a dose of 10 mg/kg.

(2) Acute toxicity test

Female Wister rats weighing about 120 g were used. A solution of Compound 1 in physiological saline was injected intraperitoneally. The dose lethal to 50% of rats ($LD_{50}$) as determined by the up-down method was 2030 mg/kg.

We claim:

1. An amide compound represented by the formula

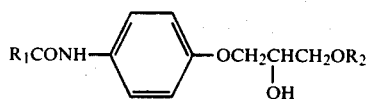

wherein $R_1$ is vinyl, 2-(methylsulfinyl)ethyl, 2-(methylsulfonyl)ethyl, 2-(2-acetylamino 2-carboxyethylthio)ethyl or 2-[2-(4-amino-4-carboxybutyrylamino)-2-(carboxymethylcarbamoyl)ethylthio]ethyl and $R_2$ is hydrogen or lower alkyl.

2. An amide compound as defined in claim 1 which is N-[4-(3-ethoxy-2-hydroxypropoxy)phenyl]acrylamide.

3. An amide compound as defined in claim 1 which is N-[4-(3-ethoxy-2-hydroxypropoxy)phenyl]-3-(methylsulfinyl)propionamide.

4. An amide compound as defined in claim 1 which is N-[4-(2,3-dihydroxypropoxy)phenyl]-3-(methylsulfinyl)propionamide.

5. An amide compound as defined in claim 1 which is N-[4-(3-ethoxy-2-hydroxypropoxy)phenyl]-3-(methylsulfonyl)propionamide.

6. An amide compound as defined in claim 1 which is N-[4-(2,3-dihydroxypropoxy)phenyl]-3-(methylsulfonyl)propionamide.

7. An amide compound as defined in claim 1 which is N-[4-(3-ethoxy-2-hydroxypropoxy)phenyl]-3-(2-acetylamino-2-carboxyethylthio)propionamide.

8. An amide compound as defined in claim 1 which is N-[4-(3-ethoxy-2-hydroxypropoxy)phenyl]-3-[2-(4-carboxybutyrylamino)-2-(carboxymethylcarbamoyl)ethylthio]propionamide.

* * * * *

UNITED STATES PATENT AND TRADEMARK OFFICE
CERTIFICATE OF CORRECTION

PATENT NO. : 4,670,583

DATED : June 2, 1987

INVENTOR(S) : KODA, Akihide; HORI, Mikio; YASUMOTO, Mitsugi; MATSUURA, Naosuke; YAMAWAKI, Ichiro; TADA, Yukio It is certified that error appears in the above-identified patent and that said Letters Patent is hereby corrected as shown below:

Claim 8, lines 2 and 3

Before "4-carboxybutrylamino..." insert --4-amino- --

Signed and Sealed this

Twenty-sixth Day of January, 1988

Attest:

DONALD J. QUIGG

Attesting Officer

Commissioner of Patents and Trademarks